United States Patent
Hong

(10) Patent No.: US 9,039,978 B2
(45) Date of Patent: May 26, 2015

(54) LOW-CARBON, MATERIAL CONSUMPTION-FREE AIR CLEANER

(76) Inventor: Kun-Liang Hong, Tainan (TW)

( * ) Notice: Subject to any disclaimer, the term of this patent is extended or adjusted under 35 U.S.C. 154(b) by 181 days.

(21) Appl. No.: 13/313,089

(22) Filed: Dec. 7, 2011

(65) Prior Publication Data

US 2013/0149200 A1 Jun. 13, 2013

(51) Int. Cl.
*A61L 9/22* (2006.01)
*B01D 53/30* (2006.01)
*B03C 3/08* (2006.01)
*B03C 3/12* (2006.01)
*B03C 3/36* (2006.01)

(52) U.S. Cl.
CPC . *B01D 53/30* (2013.01); *B03C 3/08* (2013.01); *B03C 3/12* (2013.01); *B03C 3/368* (2013.01); *B03C 2201/10* (2013.01); *A61L 9/22* (2013.01); *B01D 2257/708* (2013.01); *B01D 2257/90* (2013.01); *B01D 2257/91* (2013.01); *B01D 2259/4558* (2013.01); *B01D 2259/818* (2013.01)

(58) Field of Classification Search
CPC ............ A61L 2/14; A61L 9/22; B01D 53/30; B01D 2257/708; B01D 2257/90; B01D 2257/91; B01D 2259/4558; B01D 2259/818; B03C 3/08; B03C 3/12
USPC ............... 422/22, 120–122; 313/359.1, 362.1
See application file for complete search history.

(56) References Cited

U.S. PATENT DOCUMENTS

| | | | | |
|---|---|---|---|---|
| 4,559,467 A | * | 12/1985 | Beckmann et al. | 313/359.1 |
| 5,055,963 A | * | 10/1991 | Partridge | 361/231 |
| 7,258,723 B2 | * | 8/2007 | Crawley et al. | 95/5 |
| 2004/0140194 A1 | * | 7/2004 | Taylor et al. | 204/164 |
| 2008/0018220 A1 | * | 1/2008 | Hong | 313/359.1 |
| 2008/0035472 A1 | * | 2/2008 | Lepage | 204/229.8 |

* cited by examiner

Primary Examiner — Timothy Cleveland
(74) Attorney, Agent, or Firm — Rosenberg, Klein & Lee

(57) ABSTRACT

A low-carbon, material consumption-free air cleaner includes a rectangular box body, a fan, a negative ion generator unit and a dielectric barrier discharge actuator respectively arranged at upper part, middle part and lower part of the rectangular box body, an air input port disposed at the bottom side of the dielectric barrier discharge actuator, and air output port disposed at the top side of the rectangular box body.

2 Claims, 6 Drawing Sheets

_US 9,039,978 B2_

LOW-CARBON, MATERIAL CONSUMPTION-FREE AIR CLEANER

BACKGROUND OF THE INVENTION

1. Field of the Invention

The present invention relates air cleaning technology and more particularly, to a low-carbon, material consumption-free air cleaner.

2. Description of the Related Art

Conventional air cleaners include two types, namely, the filter type and the negative ion generator type. A filter type air cleaner may use a HEPA filter, active carbon filter, photocatalytic filer, lysozyme filter, potassium permanganate filter, potassium permanganate or ziolite filter for removing, killing bacteria, removing bad odors, and/or decomposing TVOC (total volatile organic compounds) and oil smoke. After a long use of a filter type air cleaner, the open spaces in the filter component of the filter will be clogged, and the functioning of the chemical coating of the filter will deteriorate. Thus, the filter component of the filter of a filter type air cleaner is a consumed material and must be regularly replaced, assuring normal function.

Except negative ion generator type air cleaners, commercial air cleaners commonly use filter elements for removing pollutants. These filter elements may be coated with active carbon, photocatalyst, catechin, zeolite or potassium permanganate to enhancing the power of the air cleaner in removing bad odors, killing bacteria and/or decomposing organic solvents. As these filter elements tend to be clogged, and the coated chemical substances may be saturated, oxidized or dropped, they may become a pollutant source after a long use. Further, a negative ion generator type air cleaner can only discharge negative ions in air, its effect is limited when used independently. As the discharged negative ions can be neutralized within few seconds, the effective range of a negative ion generator type air cleaner is limited.

Further, the negative ion discharging unit of a negative ion generator type air cleaner generally adopts a needle-to-plate, plate-to-plate, needle-to-hole, needle-to-needle, spot-to-spot or spot-to-circle design. However, if the applied voltage is excessively high, it may cause generation of ozone that is harmful to human body health. When a low voltage is used, the performance becomes low, not capable of discharging sufficient negative ions for purifying air.

SUMMARY OF THE INVENTION

The present invention has been accomplished under the circumstances in view. It is the main object of the present invention to provide a low-carbon, material consumption-free air cleaner, which reduces carbon production and eliminates the use of any consumed material.

To achieve this and other objects of the present invention, a low-carbon, material consumption-free air cleaner comprises a rectangular box body, a fan, a negative ion generator unit and a dielectric barrier discharge actuator respectively arranged at upper part, middle part and lower part of the rectangular box body, an air input port disposed at the bottom side of the dielectric barrier discharge actuator, and air output port disposed at the top side of the rectangular box body.

Further, the dielectric barrier discharge actuator comprises a dielectric catalyst structure, a positive electrode plate arranged at one side of the dielectric barrier discharge actuator and a negative electrode plate arranged at an opposite side of the dielectric barrier discharge actuator. The dielectric catalyst structure is shaped like a rectangular box having opposing top and bottom walls respectively formed of a mesh plate and four solid peripheral walls. The dielectric catalyst structure is made of a conducting substrate and coated with a catalytic coating selected from metal oxide or metal.

Further, the dielectric catalyst structure of the dielectric barrier discharge actuator can be made in a rectangular or cylindrical shape, or any of a variety of other shapes.

Further, the positive electrode plate and the negative electrode plate each comprise an electrically insulative planar substrate, a coating coated on the electrically insulative planar substrate, and a plurality of electrode pins perpendicularly and evenly arranged at one side of the electrically insulative planar substrate and extending out of the coating.

DETAILED DESCRIPTION OF THE INVENTION

The invention provides a low-carbon, material consumption-free air cleaner, which uses a high-power fan to draw polluted outside air into a dielectric barrier discharge module and a negative ion generator module, removing solid particles from the intake flow of air, decomposing TVOC (total volatile organic compounds) and oil smoke in the intake flow of air, removing bad odors from the intake flow of air, and killing bacteria in the intake flow of air.

Figure 1:
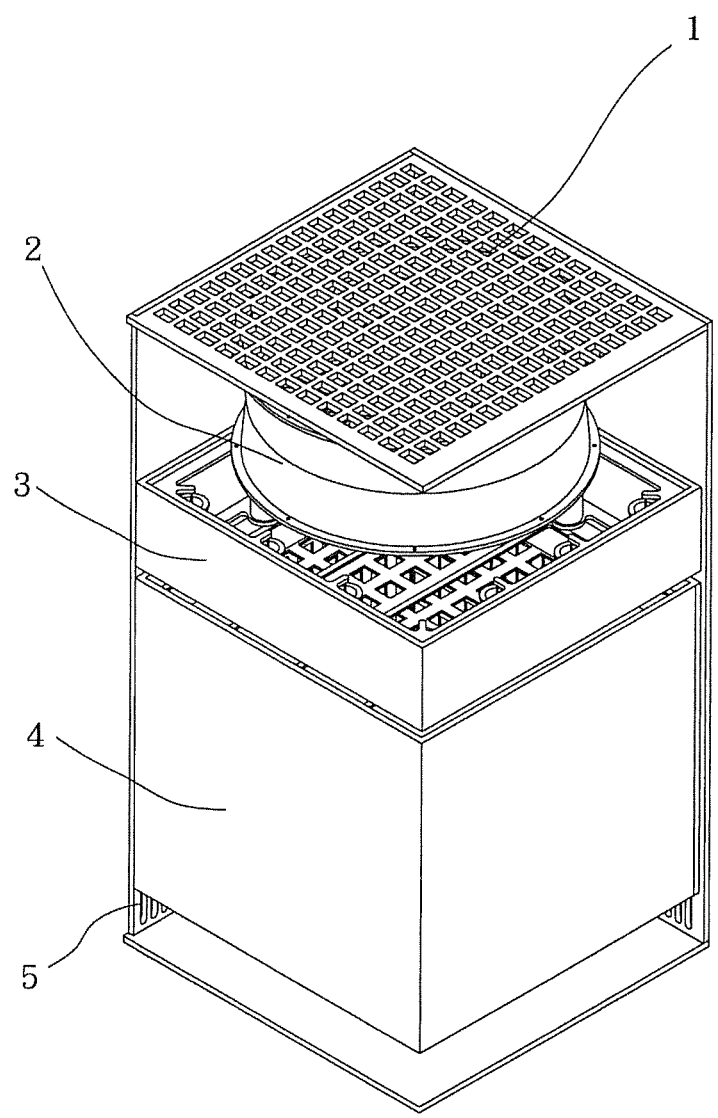
FIG. 1 is an elevational view of a low-carbon, material consumption-free air cleaner in accordance with the present invention.
Figure 4:
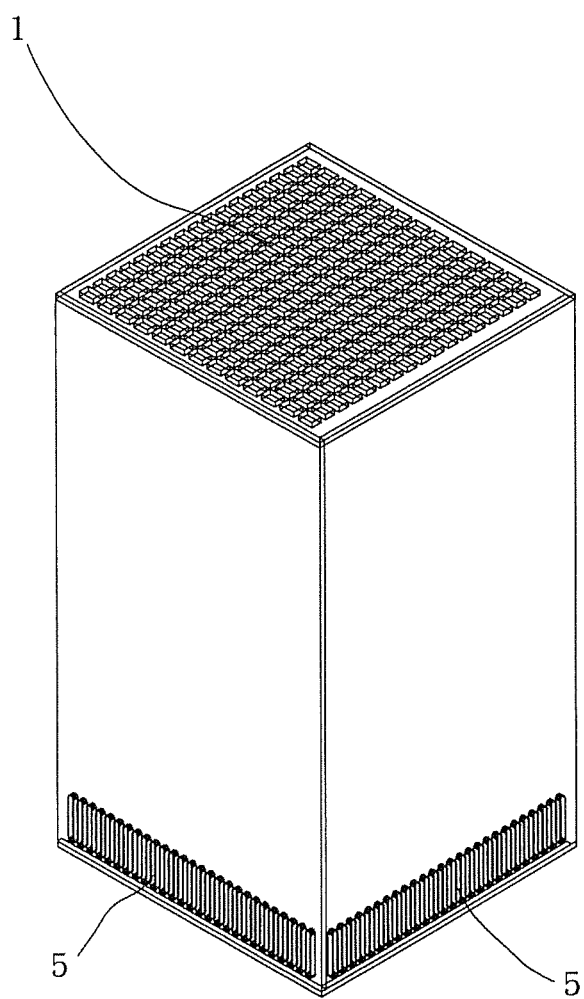
FIG. 4 illustrates the outer appearance of the low-carbon, material consumption-free air cleaner in accordance with the present invention.

The body of the low-carbon, material consumption-free air cleaner is shaped like a rectangular upright box, as shown in FIG. 4. The low-carbon, material consumption-free air cleaner comprises a dielectric barrier discharge actuator 4, a negative ion generator unit 3, a fan 2, an air input port 5, and an air output port 1. The fan 2, the negative ion generator unit 3 and the dielectric barrier discharge actuator 4 are respectively arranged at the upper part, middle part and lower part of the rectangular box body of the low-carbon, material consumption-free air cleaner. The air input port 5 is disposed at the bottom side of the dielectric barrier discharge actuator 4, i.e., the bottom side of the low-carbon, material consumption-free air cleaner. The air output port 1 is disposed at the top side of the low-carbon, material consumption-free air cleaner. When the fan 2 is started, the inside space of the rectangular box body of the low-carbon, material consumption-free air cleaner is changed to a vacuum status, drawing in outside air through the air input port 5 toward the air output port 1 via the dielectric barrier discharge actuator 4 and the negative ion generator unit 3. The structure of the low-carbon, material consumption-free air cleaner is shown in FIG. 1.

Figure 3:
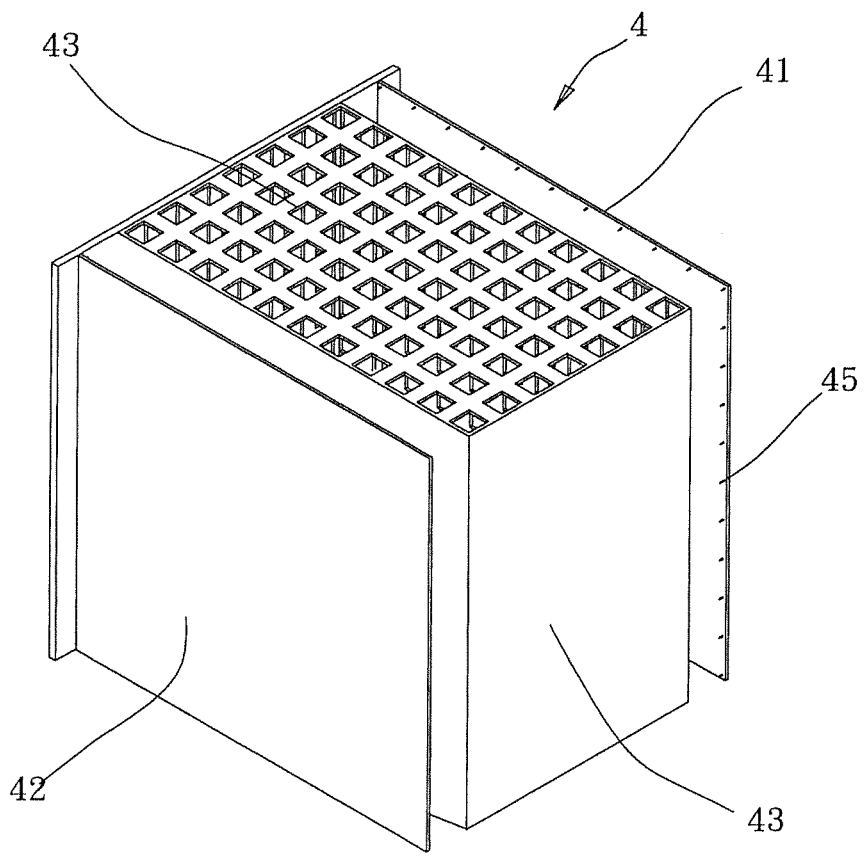
FIG. 3 illustrates the structure of the dielectric barrier discharge actuator of the low-carbon, material consumption-free air cleaner in accordance with the present invention.
Figure 7:
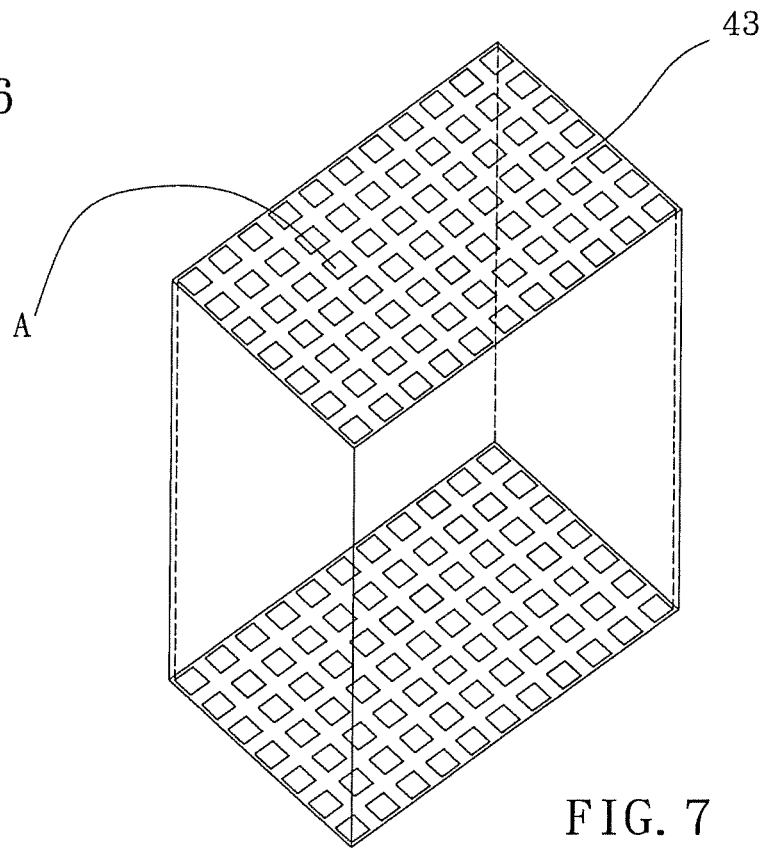
FIG. 7 is a schematic drawing of the present invention, illustrating the design of the dielectric catalyst structure of the dielectric barrier discharge actuator.
Figure 8:
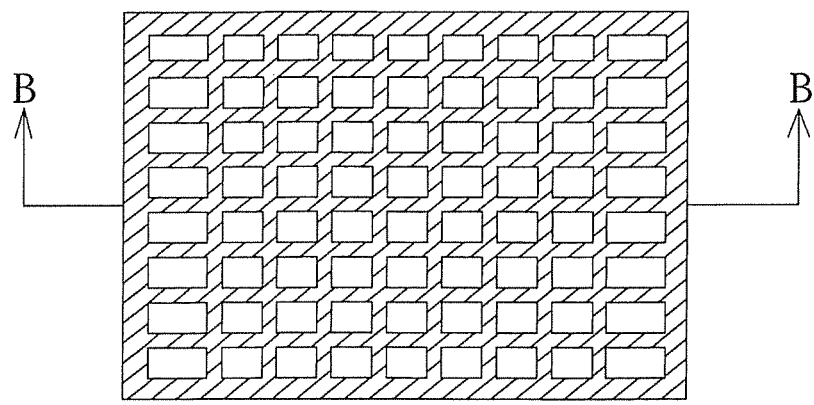
FIG. 8 illustrates the structure of a mesh plate forming each of the opposing top and bottom walls of the dielectric catalyst structure of the dielectric barrier discharge actuator.
Figure 9:
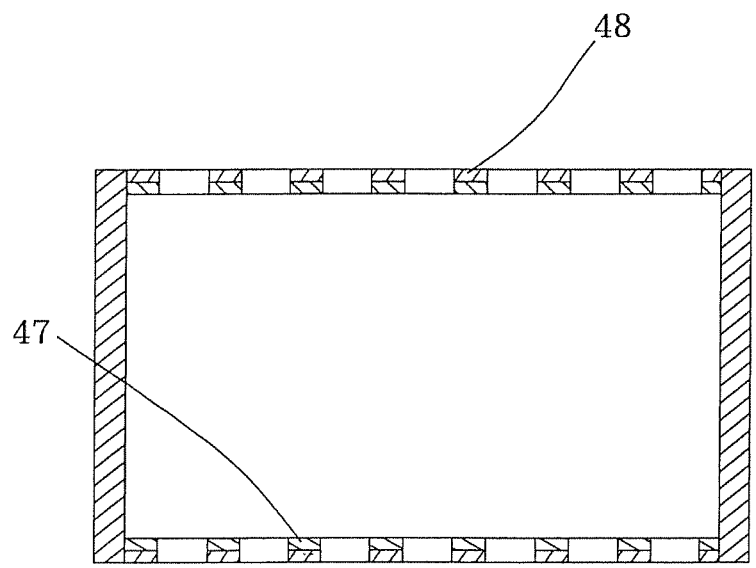
FIG. 9 is a sectional view taken along line B-B of FIG. 8.

The dielectric barrier discharge actuator 4, as shown in FIG. 3, comprises a positive electrode plate 41, a negative electrode plate 42, and a dielectric catalyst structure (see FIG. 7). The positive electrode plate 41 and the negative electrode plate 42 are arranged at two opposing sides of the dielectric catalyst structure. The dielectric catalyst structure is shaped like a rectangular box having opposing top and bottom walls respectively formed of a mesh plate A and four solid peripheral walls, as shown in FIG. 8. The dielectric catalyst structure is made of a conducting substrate 48 and coated with catalytic coating 47 (metal oxide or metal). The catalytic coating 47 covers the whole inner surface of the dielectric catalyst structure (see FIG. 9). Thus, a meshed dielectric barrier discharge actuation structure 43 is formed. When the positive electrode plate 41 and the negative electrode plate 42 of the dielectric barrier discharge actuator 4 are electrically connected, the catalytic coating 47 (metal oxide or metal) of the dielectric catalyst structure is caused to turn into positive ions for decomposing pollutants in the intake flow of air. It is to be understood that the dielectric catalyst structure could be made in a rectangular or cylindrical shape, or any of a variety of other shapes.

The positive electrode plate 41 and negative electrode plate 42 of the dielectric barrier discharge actuator 4 give positive/negative high voltage to the dielectric catalyst structure, causing the dielectric catalyst structure to discharge charges, and therefore positive ions and negative ions are neutralized rapidly in the dielectric catalyst structure. At this time, ions are conducting in the dielectric of the dielectric catalyst structure. As the dielectric of the dielectric catalyst structure is a good conductor, the dielectric catalyst structure discharges charges uniformly, producing a strong discharge energy that effectively decomposes organic substances in the intake flow of air, killing all bacteria and decomposing all oil smoke.

Figure 2:
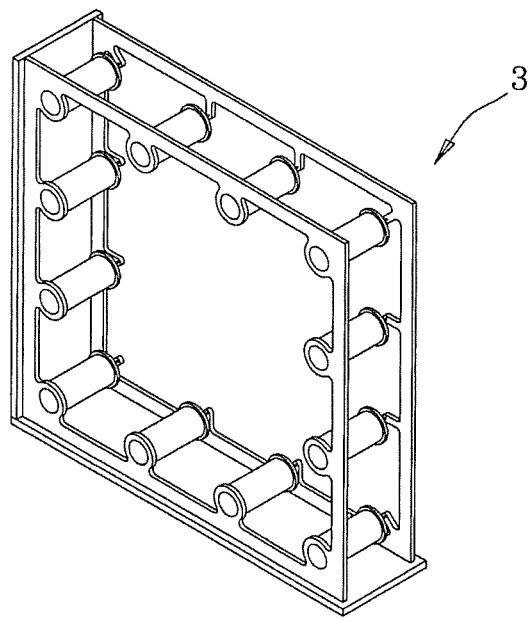
FIG. 2 illustrates the structure of the negative ion generator unit of the low-carbon, material consumption-free air cleaner in accordance with the present invention.

The negative ion generator unit 3 at the top side of the dielectric barrier discharge actuator 4 is a hollow endless structure, as shown in FIG. 2. The negative ion generator unit 3 is configured subject to the configuration of the dielectric barrier discharge actuator 4, carrying a plurality of negative ion generators around the periphery.

Figure 5:
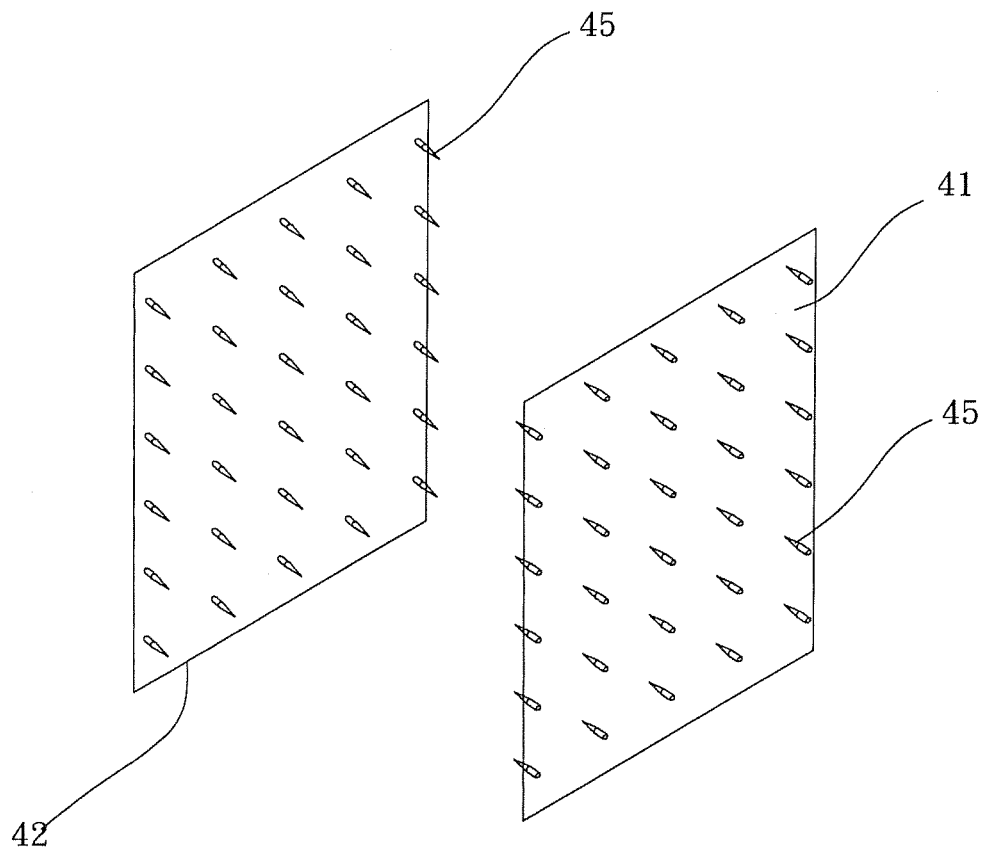
FIG. 5 is a schematic drawing of the present invention, illustrating the structure of the positive electrode plate and negative electrode plate.
Figure 6:
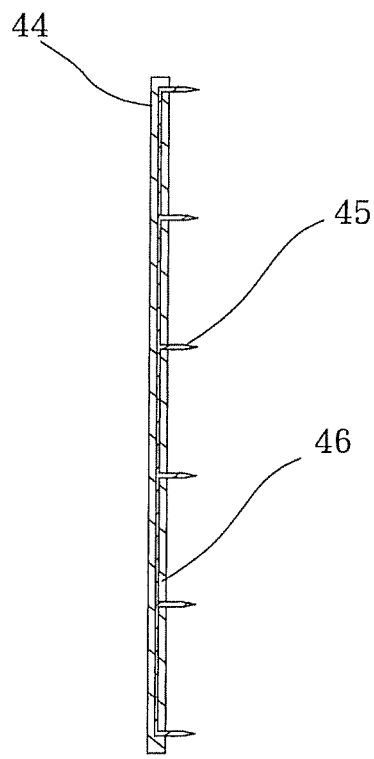
FIG. 6 is a schematic sectional view of one electrode plate for the low-carbon, material consumption-free air cleaner in accordance with the present invention.

The structure of the positive electrode plate 41 and the structure of the negative electrode plate 42 are shown in FIGS. 5 and 6. As shown in FIG. 7, the positive electrode plate 41 and the negative electrode plate 42 are arranged at two opposing sides of the dielectric catalyst structure of the dielectric barrier discharge actuator 4. Each of the positive electrode plate 41 and negative electrode plate 42 comprises an electrically insulative planar substrate 44, a coating 46 coated on the electrically insulative planar substrate 44, and a plurality of electrode pins 45 perpendicularly and evenly arranged at one side of the electrically insulative planar substrate 44 and extending out of the coating 46. After installation, the electrode pins 45 of the positive electrode plate 41 are respectively aimed at the electrode pins 45 of the negative electrode plate 42.

The operation of the low-carbon, material consumption-free air cleaner is outlined hereinafter. When the low-carbon, material consumption-free air cleaner is electrically connected to start the fan 2, the fan 2 draws air out of the low-carbon, material consumption-free air cleaner, causing the internal space of the low-carbon, material consumption-free air cleaner to be changed into a vacuum status that sucks in outside air through the air input port 5 toward the air output port 1 via the dielectric barrier discharge actuator 4 and the negative ion generator unit 3. At this time, high power discharge energy from the dielectric barrier discharge actuator 4 decomposes organic substances and oil smoke in the intake flow of air and kills bacteria. The air purified by the dielectric barrier discharge actuator 4 keeps flowing toward the air input port 5 through the negative ion generator unit 3 to carry discharged negative ions from the negative ion generator unit 3 to the outside of the low-carbon, material consumption-free air cleaner.

When compared with conventional air cleaners, the low-carbon, material consumption-free air cleaner that is formed of the aforesaid dielectric barrier discharge actuator 4, negative ion generator unit 3, fan 2, air input port 5 and air output port 1 does no require replacement of any consumption material. The low-carbon, material consumption-free air cleaner of the present invention effectively decomposes organic substances and oil smoke in the intake flow of air and kills bacteria, adding negative ions to the purified output air.

In conclusion, the invention provides a low-carbon, material consumption-free air cleaner, which comprises a dielectric barrier discharge actuator 4, a negative ion generator unit 3, a fan 2, an air input port 5, and an air output port 1, wherein the fan 2, the negative ion generator unit 3 and the dielectric barrier discharge actuator 4 are respectively arranged at the upper part, middle part and lower part of the rectangular box body of the low-carbon, material consumption-free air cleaner; the air input port 5 is disposed at the bottom side of the dielectric barrier discharge actuator 4, i.e., the bottom side of the low-carbon, material consumption-free air cleaner; the air output port 1 is disposed at the top side of the low-carbon, material consumption-free air cleaner. When the fan 2 is started, the inside space of the rectangular box body of the low-carbon, material consumption-free air cleaner is changed to a vacuum status, drawing in outside air through the air input port 5 toward the air output port 1 via the dielectric barrier discharge actuator 4 and the negative ion generator unit 3.

The dielectric barrier discharge actuator 4 is a rectangular device comprising a dielectric catalyst structure, and opposing positive electrode plate 41 and negative electrode plate 42 respectively arranged at two opposing sides of the dielectric catalyst structure. When the positive electrode plate 41 and the negative electrode plate 42 are electrically connected, the dielectric catalyst structure is caused to discharge charges to neutralize and decompose organic substances and oil smoke in the intake flow of air and to kill bacteria, purifying the air.

When the low-carbon, material consumption-free air cleaner is electrically connected to start the fan 2, the fan 2 draws air out of the low-carbon, material consumption-free air cleaner, causing the internal space of the low-carbon, material consumption-free air cleaner to be changed into a vacuum status that sucks in outside air through the air input port 5 toward the air output port 1 via the dielectric barrier discharge actuator 4 and the negative ion generator unit 3. At this time, high power discharge energy from the positive electrode plate 41 and negative electrode plate 42 of the dielectric barrier discharge actuator 4 decomposes organic substances and oil smoke in the intake flow of air and kills bacteria. The air purified by the dielectric barrier discharge actuator 4 keeps flowing toward the air input port 5 through the negative ion generator unit 3 to carry discharged negative ions from the negative ion generator unit 3 to the outside of the low-carbon, material consumption-free air cleaner.

What is claimed is:

1. A low-carbon, material consumption-free air cleaner, comprising:

a rectangular box body, a dielectric barrier discharge actuator, a negative ion generator unit, a fan, an air input port and an air output port, said air input and output ports defining an air flow path therebetween;

said fan, said negative ion generator unit and said dielectric barrier discharge actuator being disposed in the air flow path respectively arranged at upper part, middle part and lower part of said rectangular box body, said air input port being disposed at a bottom side of said dielectric barrier discharge actuator, said air output port being disposed at a top side of said rectangular box body wherein said fan creates a pressure drop within said rectangular box body, said fan mounted on an upper surface of said negative ion generator unit and sandwiched between said negative ion generator unit and said air output port;

wherein said dielectric barrier discharge actuator includes positive and negative electrode plates disposed in opposing manner about said air flow path, each of said electrode plates having a catalytic coating formed on an insulative planar substrate and a plurality of mesh plates extending transversely across said air flow path, each of said mesh plates including a conductive structure having said catalytic coating;

whereby said air flow path is unimpeded between said mesh plates and said fan;

wherein said dielectric barrier discharge actuator comprises a dielectric catalyst structure, said positive electrode plate arranged at one side of said dielectric catalyst structure and said negative electrode plate arranged at an opposite side of said dielectric catalyst structure, said dielectric catalyst structure substantially defining a rectangular box having opposing top and bottom walls each formed by one of said mesh plates and four solid peripheral walls, said dielectric catalyst structure being made of said conductive structure having said catalytic coating, said coating selected from metal oxide or metal.

2. The low-carbon, material consumption-free air cleaner as claimed in claim 1, wherein said positive electrode plate and said negative electrode plate each comprise a plurality of electrode pins perpendicularly and evenly arranged at one side of each said electrically insulative planar substrate and extending out of said coating.

* * * * *